United States Patent [19]

Oxland et al.

[11] Patent Number: 5,676,666
[45] Date of Patent: Oct. 14, 1997

[54] CERVICAL SPINE STABILIZATION SYSTEM

[75] Inventors: Thomas R. Oxland, Bloomington; Douglas W. Kohrs, Edina; Donald Erickson, Stillwater; Paul Sand, Roseville, all of Minn.

[73] Assignee: SpineTech, Inc., Minneapolis, Minn.

[21] Appl. No.: 619,167

[22] Filed: Mar. 21, 1996

Related U.S. Application Data

[63] Continuation of Ser. No. 294,377, Aug. 23, 1994, abandoned.

[51] Int. Cl.$^6$ ................................................. A61B 17/70
[52] U.S. Cl. .................................................. 606/61; 606/73
[58] Field of Search ............................. 606/61, 69, 72, 606/73, 86, 205, 96

[56] References Cited

U.S. PATENT DOCUMENTS

| | | | |
|---|---|---|---|
| 976,847 | 11/1910 | Chambalin | 411/307 |
| 2,460,470 | 2/1949 | Rogers | 606/86 |
| 3,146,142 | 8/1964 | Maly | 411/258 |
| 4,461,305 | 7/1984 | Cibley. | |
| 4,502,475 | 3/1985 | Weigle et al. | 606/86 |
| 4,696,290 | 9/1987 | Steffee. | |
| 4,763,644 | 8/1988 | Webb. | |
| 4,822,366 | 4/1989 | Bolesky. | |
| 4,836,196 | 6/1989 | Park et al.. | |
| 4,913,134 | 4/1990 | Luque. | |
| 5,030,200 | 7/1991 | Howland. | |
| 5,084,048 | 1/1992 | Jacob et al.. | |
| 5,084,049 | 1/1992 | Asher et al.. | |
| 5,085,660 | 2/1992 | Lin. | |
| 5,092,893 | 3/1992 | Smith. | |
| 5,108,399 | 4/1992 | Eitenmuller et al. | 606/73 |
| 5,127,912 | 7/1992 | Ray et al.. | |
| 5,129,899 | 7/1992 | Small et al.. | |
| 5,129,900 | 7/1992 | Asher et al.. | |
| 5,151,103 | 9/1992 | Tepic et al.. | |
| 5,171,279 | 12/1992 | Mathews. | |
| 5,176,679 | 1/1993 | Lin. | |
| 5,234,431 | 8/1993 | Keller. | |
| 5,261,910 | 11/1993 | Warden et al.. | |
| 5,269,784 | 12/1993 | Mast. | |
| 5,282,862 | 2/1994 | Baker et al.. | |
| 5,282,863 | 2/1994 | Burton. | |
| 5,318,589 | 6/1994 | Lichtman. | |

*Primary Examiner*—Michael Buiz
*Assistant Examiner*—Daphna Shai
*Attorney, Agent, or Firm*—Vidas, Arrett & Steinkraus, P.A.

[57] ABSTRACT

A method and device for stabilizing cervical vertebrae includes a plate with at least two slots. The device also includes at least two screws including a lower threaded bone-engaging shaft, a shoulder which will not pass through said plate slots and an upper threaded shaft. The screws are positioned and the plate rests on top of the screw shoulders. Locking, low profile caps secure the plate to the screws.

2 Claims, 6 Drawing Sheets

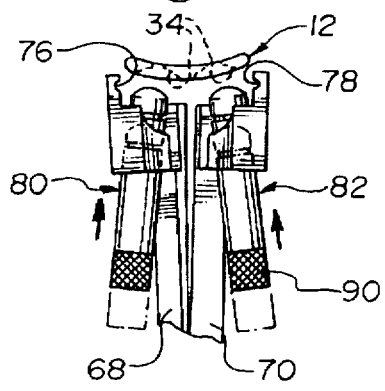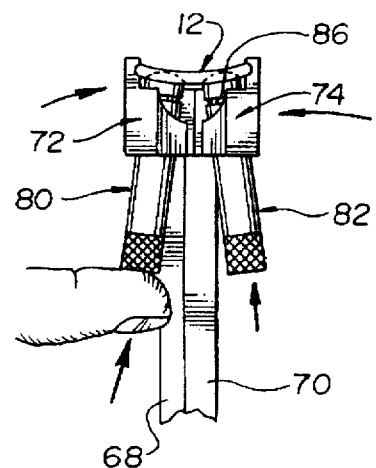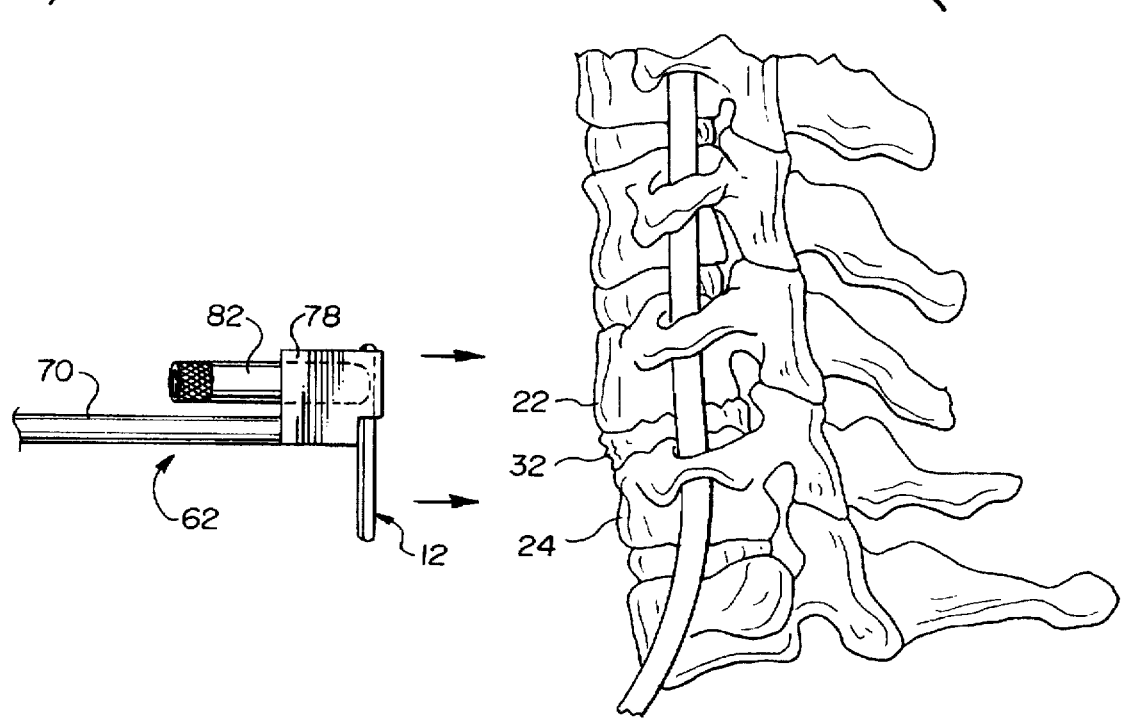

5,676,666

CERVICAL SPINE STABILIZATION SYSTEM

This application is a continuation of application Ser. No. 08/294,377, filed Aug. 23, 1994, now abandoned.

BACKGROUND OF THE INVENTION

1. Field of the Invention

This invention relates to a system for stabilizing cervical vertebrae of the neck.

2. Description of the Related Art

Asher et al., U.S. Pat. No. 5,084,049 shows spine plates with a plurality of openings, each with semispherical recesses. Each fastener includes a bone screw with a shoulder to space the plate from the vertebrae. The nut includes a portion 56 to engage the semispherical recess.

Luque, U.S. Pat. No. 4,913,134 includes screws with a convex head shape sized to fit into concave depressions in a plate. The upper portion of the head may be snapped off for a lower profile. The plate has elongated holes. The screw heads are above the plate and could back out if not for an overcap lock.

Small et al, U.S. Pat. No. 5,129,899 is of interest in its showing of an elongated plate, bone screw with shoulder larger than the plate opening and nuts with a relatively low profile. A load transfer washer 35 is required.

Lin, U.S. Pat. No. 5,176,679 is of interest in its method of use. It may use the plate with assembled sleeves as a guide for drilling. The guide is then removed and the screws are inserted. The guide with sleeves is then positioned on top of and to the screws.

Warden et al, U.S. Pat. No. 5,261,910 has a plate which requires a seat and is constructed to ensure that rotation between the plate and fastener is not possible.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY OF THE INVENTION

The invention provides a method and apparatus which provide intervertebral stabilization with a very low profile and positive locking while providing anatomic flexibility. Basically, the invention consists of a cervical plate having at least two slots. The plate is connected to adjacent vertebrae to provide stabilization and eventually fuse the vertebrae. The plate slots are designed to include an upper recessed area into which a mating lock cap may fit in a very low profile. The plate is secured to bone of the vertebrae by at least two unique screws. The lock cap-screw combination may be positioned anywhere along the length of the slot. The screws are designed to have a threaded, bone engaging shaft, an enlarged shoulder and an upper threaded shaft which accepts the lock cap. The plate is positioned over the shoulder of screws already screwed into bone. The shoulder is sized such that the screw cannot pass through the plate slot.

Preferably, a combination plate holder/guide is used to align the plate on the spine and guide formation of the screw holes. The screws are placed into the vertebrae and the plate is positioned over the screw, against the screw shoulders. The locking caps are attached to complete the stabilization procedure.

A template of similar shape to the plate but with slots large enough to pass the screw shoulders may be used to guide formation of the screw holes and placement of the screws. The template is then removed and the plate is positioned over the screw, resting against the screw shoulders. The lock caps are then attached to complete the stabilization procedure.

BRIEF DESCRIPTION OF THE DRAWINGS

A detailed description of the invention is hereafter described with specific reference being made to the drawings in which:

FIG. 1a is a front fragmentary view thereof showing an adjustment screw;

FIG. 1b is a perspective view thereof illustrating the positioning pins;

FIG. 1c is a cut away sectional view thereof taken along line 1c—1c of FIG. 1b showing the positioning rings;

FIG. 4 is a top elevational view thereof demonstrating the grasping of the cervical plate with the clamp;

FIG. 5 is a top elevational view thereof demonstrating the plate grasped with the clamp;

FIG. 6 is a side elevational thereof showing the plate being positioned;

DESCRIPTION OF THE PREFERRED EMBODIMENTS

With reference to the figures, it will be seen that the device 10 of the invention includes a cervical plate 12, bone screws 14 and locking caps 16.

Figure 3:
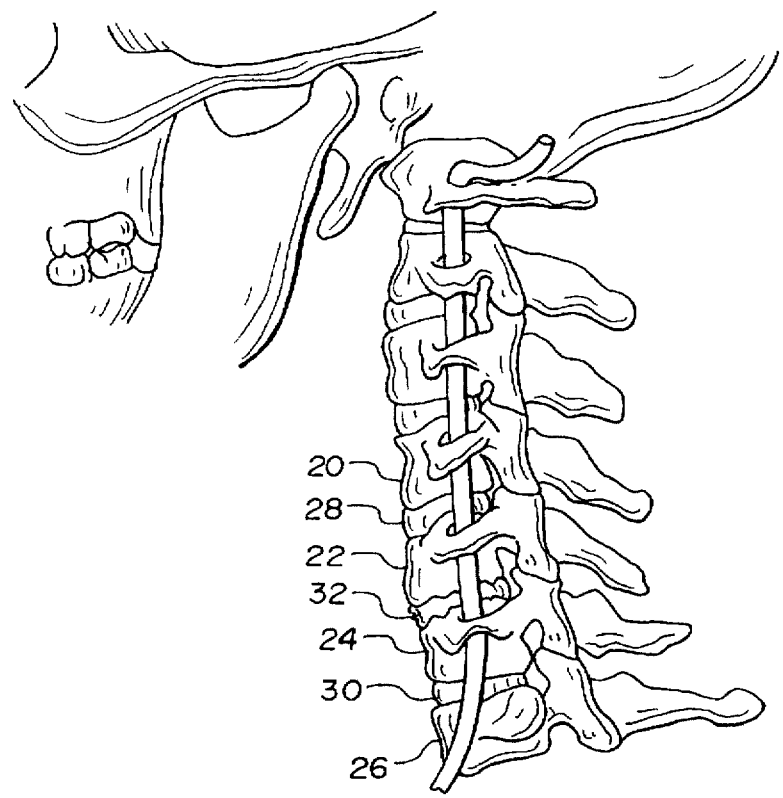
FIG. 3 is a side elevational view thereof showing a cervical spine with a damaged disc.

The cervical fusion device 10 of the invention is best described with reference to its use. FIG. 3 shows a typical spinal segment consisting of vertebrae 20, 22, 24, 26. Normal, healthy discs 28, 30 are shown as well as a damaged disc 32. Further, the ligaments between vertebrae 22 and 24 may be damaged resulting in an unstable segment. Fusion of vertebrae 22 to 24 is one method of dealing with these pathologic conditions.

With reference to FIGS. 2, 4, 5, 7–11, 12 and 14 it will be seen that cervical plate 12 is a machined, curved plate, typically of biocompatible metal with a plurality of openings 34 therethrough. Plate 12 has an upper surface 36 and a lower, bone contacting surface 38. Openings 34 are constructed such that the area of the opening on the upper surface 36 is larger than the area on the lower, bone contacting surface 38. The bottom of the plate may be curved or have flats.

Figure 9:
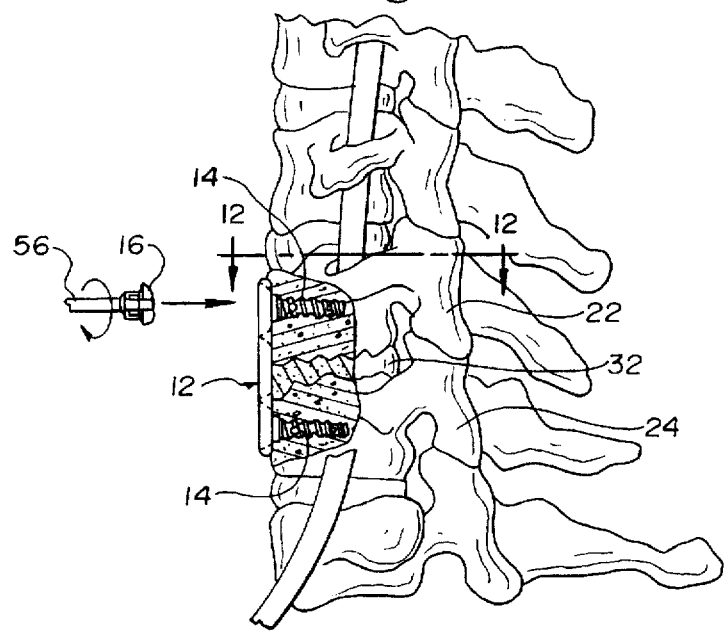
FIG. 9 is a side elevational view thereof with the bone screws inserted and cap being positioned.
Figure 12:
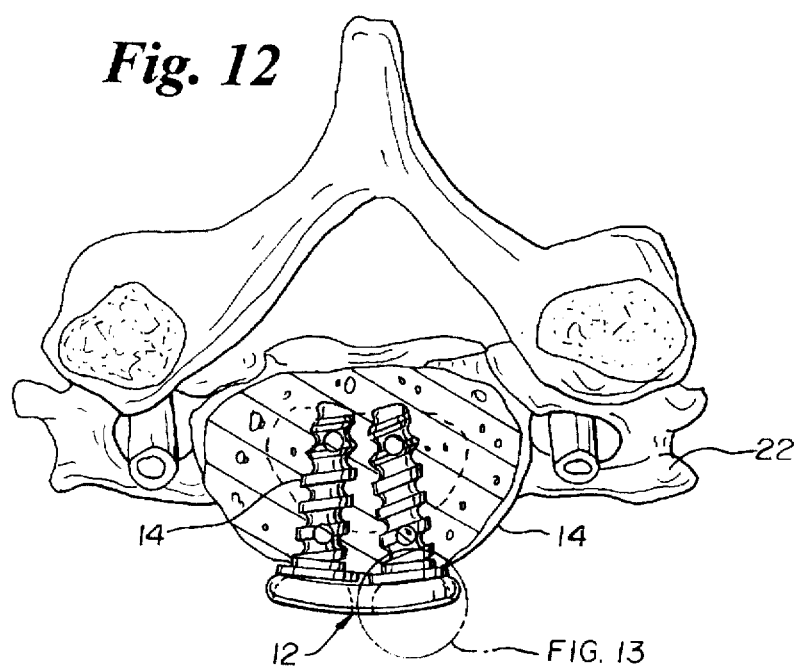
FIG. 12 is a cross-sectional view showing the profile of the installed plate.

Bone screws 14 include a lower threaded shaft 40 that is screwed into bone as shown in FIGS. 9 and 12. Bone screws 14 include an upper threaded shaft 42 that engage with locking caps 16. In between is an enlarged shoulder 44 which is sized such that it may not pass through openings 34. Bone screws 14 may have a plurality of transverse holes to facilitate osseointegration.

Figure 1:
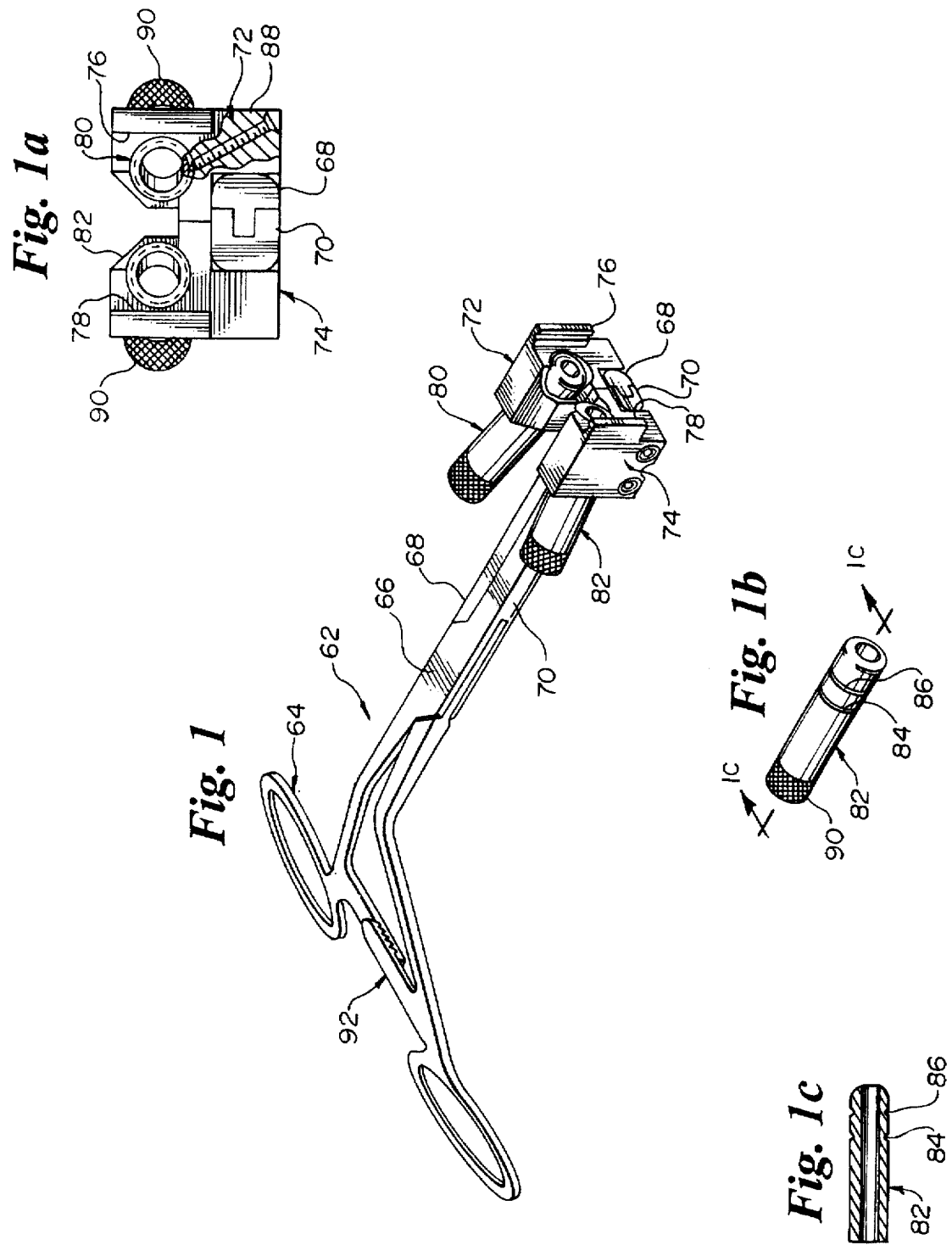
FIG. 1 is a perspective view of a plate clamp of the invention.

The preferred installation of cervical plate 12 is through the use of a plate holder/guide clamp 62 as shown in FIGS. 1 and 4-7. As best shown in FIG. 1, clamp 62 is a modified fixation forceps including a handle 64, pivot joint 66 and blades 68, 70. Each blade includes a guide head 72, 74 with opposing lips 76, 78 which attach to plate 12 as shown in FIG. 5. Guide cylinders 80, 82 are slidably positionable in each guide head 72, 74 at the required angle. Guide cylinders 80, 82 may include positioning rings 84, 86 which may engage with a detent 88. This allows the depth of the guide cylinders 80, 82 to be readily selected. Guide cylinders 80, 82 may include knurling 90 at an end to make manual adjustment easier. In addition, a typical forceps lock mechanism 92 may be employed.

In operation, tool 62 is used as shown in FIGS. 4-7. First, the tool 62 is opened as in FIG. 4 to grasp a device 10 between the opposing lips 76, 78. The guide cylinders 80, 82 are pushed down to contact with the openings 34 in the plate 12 as in FIG. 5. The positioning rings 84, 86 allow for change in depth. Once the proper alignment is made, the tool 62 may be locked with the forceps lock 92.

Figure 7:
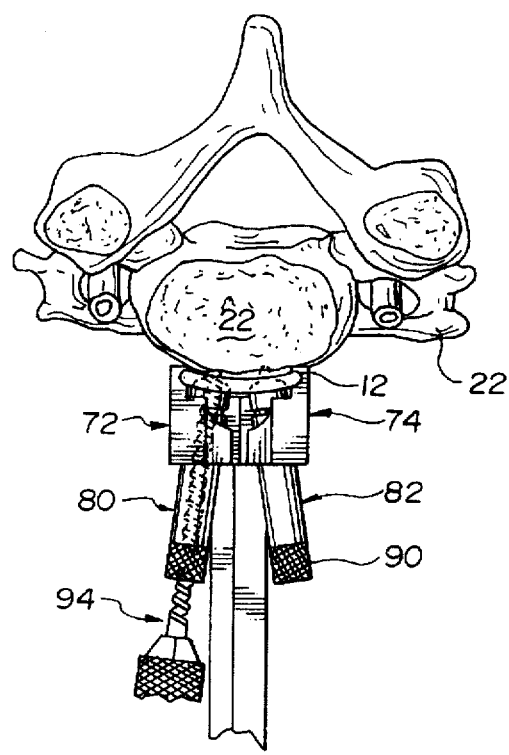
FIG. 7 is a top elevational view thereof illustrating the formation of screw holes.
Figure 8:
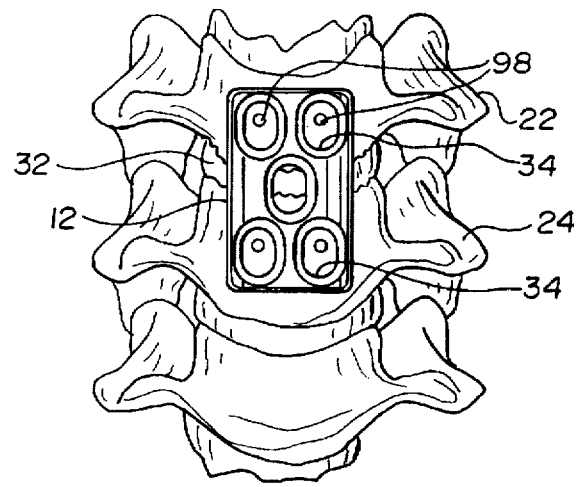
FIG. 8 is a from elevational view thereof showing the plate in position with the formed screw holes.

The device 10, now firmly held to the tool 62, is brought to bear against a cervical vertebrae as illustrated in FIGS. 6 and 7. Once in position, pilot holes for the self-tapping screws 14 may be formed. Preferably, as shown, a drill 94 placed through a guide cylinder is used to form the pilot holes needed. The depth of drilling is controlled to prevent penetration into the spinal cord. Alternatively, an awl may take the place of the drill. FIG. 8 shows the plate 12 with pilot holes 98 shown in relation to the slotted openings 34 of the plate 12.

Figure 11:
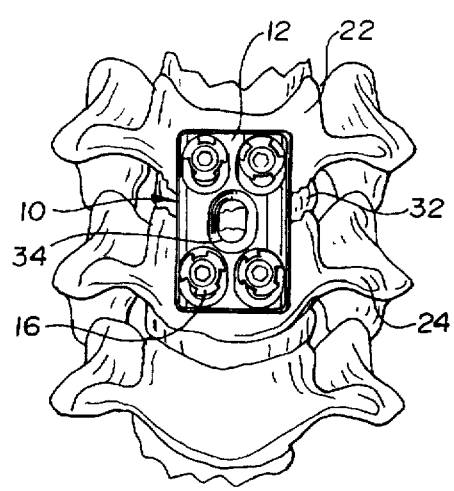
FIG. 11 is a front elevational view of the installed plate.
Figure 13:
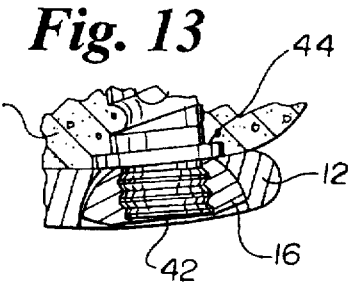
FIG. 13 is a greatly enlarged view of the interface of cap, screw and plate taken from FIG. 12.

FIG. 9 shows that the tool 62 has been removed, screws 14 have been inserted, plate 12 has been positioned over the screws 14 and an insertion tool 56 is shown ready to position locking cap 16. FIG. 11 shows the fully installed device 10 which stabilizes the adjacent vertebrae. FIGS. 12 and 13 show the extremely low profile of the installed device 10.

Figure 10:
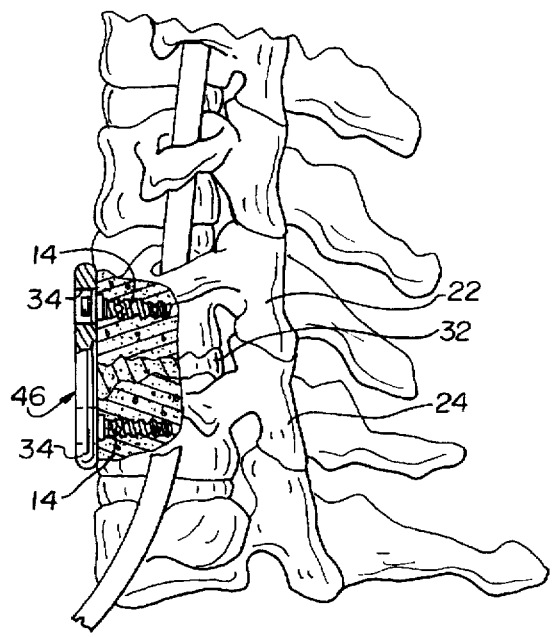
FIG. 10 is a side elevational view thereof showing a template with larger holes.

In operation, it is possible to install the device with the aid of a template 46 as shown in FIG. 10. The template 46 is constructed to include the same spaced holes or openings 34 as in the cervical plate 12. The template 46 has openings 34 that will allow passage of the bone screws 14 including the shoulders 44. Template 46 may appear identically to plate 12 except for the size of openings 34 which in template 46 are larger.

Figure 2:
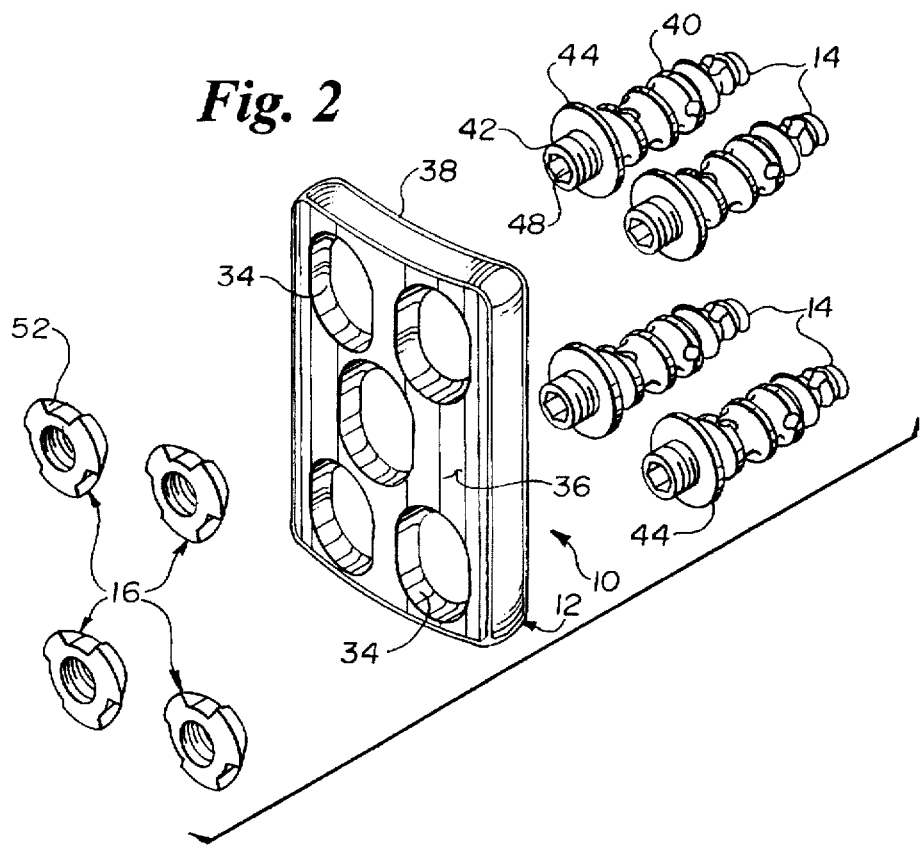
FIG. 2 is an exploded perspective view thereof illustrating the plate, locking caps and screws.

The template 46 is positioned where desired and holes are prepared for the screws. The screws may then be fully inserted with the template guide in place until their shoulders 44 abut against the bone. Typically bone screws 14 would be installed by means of a hex head 48 connecting to an allen wrench. This hex head 48 as shown in FIG. 2 provides an internal tool receiving means for the allen wrench. The template allows accurate positioning of the screws and is then removed.

Next, the cervical plate 12 is positioned over the bone screws 14 until it abuts against the shoulders 44. The plate 12 is locked to the screws 14 by locking caps 16 as shown. The locking caps are preferably threaded such that the cap tends to be locked in place. One way is to use the threads sold under the designation SPIRALOCK™ brand threads in which the female threads are slightly different from the male threads. Detroit Tool Industries of Madison Heights, Mich. produces such locking threads. Thread locking compounds may also be used to prevent loosening of the caps. The caps 16 may include a head configuration 52 that allows the use of an insertion tool 56 which may grip and turn the cap 16.

Figure 14:
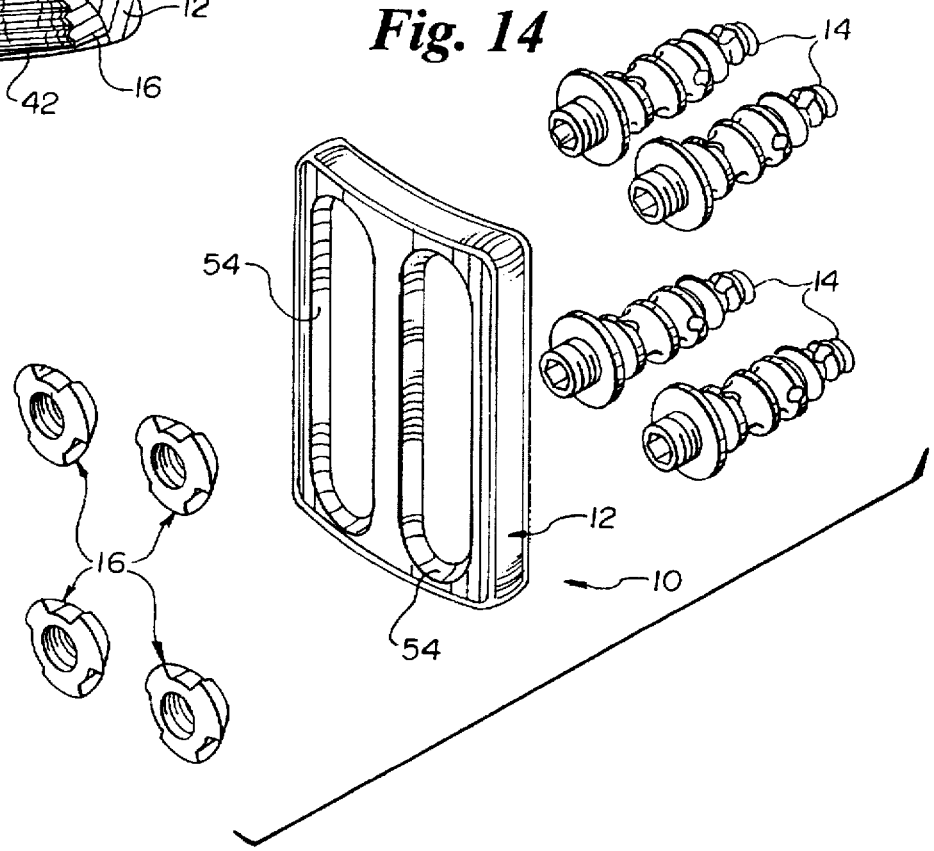
FIG. 14 is a perspective view of an alternative plate with elongated slots in the plate.

FIG. 14 shows that the device 10 of the invention may include a plate 12 having elongated openings 54 rather than openings 34. The openings 54 would still be slightly larger at the upper surface 36 than the lower surface 38 to ensure that the shoulder 44 may not pass therethrough and to provide a cavity into which the cap 16 may fit. The elongated slot allows the physician more latitude in placing the screws, since they may be anywhere within the long slots. Obviously, any combination of conventional openings 34 and elongated openings 54 may be employed. Generally, it may be advantageous to make each opening 34 in the plate 12 somewhat elongated along one direction to provide for minor adjustments.

Usually, plate 12 will not be flat and will have a bend conforming to the vertebrae to which it will be affixed. Plate benders may be employed during surgery to bend the plate to a custom fit to the patient. In such a case, normal round openings may be made off-round, no longer accommodating a screw. For this reason, the slightly to greatly elongated openings 34, 54 of the invention allows the screws to fit even after bending the plate. If one screw does not line up properly with the plate, it may be removed. The device is then installed without that screw and a conventional non-shouldered screw may be inserted from the upper surface 36 of the plate 12.

Although the device may be installed with the aid of a template, no template is required. If desired, the cervical plate 12 may be used as a template, although it would need to be removed so the screws can be installed permanently.

In general, the screws 14 are self-tapping and the step of tapping holes for the screws is not needed. The figures show the stabilization of two adjacent vertebrae by the device of the invention. The plate may be extended in length such that more than two vertebrae are fused together. That is, three or more vertebrae could be fused by a single, longer plate 12 with screws locking into each vertebrae.

As shown in the drawings, the installed stabilization device 10 has a very low profile without protruding screws. The construction greatly decreases the possibility of the screws backing out and contacting any vulnerable structure.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A device for stabilizing cervical vertebrae comprising:
 (a) an elongated, bendable bone plate having an upper and a lower surface, said plate including a plurality of elongated slots through said plate, said slots defining a larger opening at said entire upper surface than at said lower surface;

(b) a bone screw comprising a lower threaded bone engaging shaft, an upper threaded shaft sized to pass through said bone plate slots said upper threaded shafts including internal tool receiving means into which a tool may be inserted to apply turning force to the screw, an enlarged diameter, but narrow height shoulder situated between said lower and upper shafts, said shoulder being larger in diameter than said upper and lower shafts such that said shoulder may not pass through said slots; and (c) a lock cap including threads to mate with said bone screw upper shaft, said cap including a top surface and a bottom surface and being constructed and arranged to taper in diameter from said top surface to said bottom surface, with the bottom diameter being smaller than the top diameter to thereby substantially fit within said upper surface of said slots of said plate without passing therethrough said slots and to lock said screw to said plate, said bendable plate allowing said plate to be bent as required to adapt to a patient, said elongated slots providing openings through which said caps will pass into before and after bending of said plates, said elongated slots being constructed and arranged such that said lock cap may be seated therewithin anywhere throughout the length of said slot.

2. A method for stabilizing cervical vertebrae together with a plate, the method comprising the steps of:

(a) holding a cervical plate having a plurality of spaced slots with a hand held guide clamp, said guide clamp including clamping members for holding a cervical plate, said guide clamp further including at least one guide cylinder through which tools may be inserted;

(b) aligning said guide clamp and cervical plate such that one of said at least one guide cylinder is positioned directly over one of said spaced plate slots;

(c) placing said plate held with said guide clamp against a vertebral segment to be stabilized;

(d) marking positions for screws to be screwed into said vertebral segments on bone of said cervical vertebra by passing a marking instrument through said guide cylinder and then removing said plate, guide clamp and guide cylinder from the vertebra;

(e) screwing in a screw into each marked position for a bone screw, each said screw including a lower threaded shaft, an intermediate shoulder and an upper threaded shaft;

(f) positioning said cervical plate or a different cervical plate, each having a plurality of elongated slots arranged to mate with each of said screw upper shafts over said shafts, each of said slots being sized such that said screw shoulder may not pass therethrough; and (g) locking said cervical plate to said screws by affixing overcaps to said upper threaded shafts, thereby stabilizing said vertebrae.

* * * * *